US009678217B2

(12) United States Patent
Therriault-Proulx et al.

(10) Patent No.: US 9,678,217 B2
(45) Date of Patent: Jun. 13, 2017

(54) METHODS AND APPARATUS FOR OPTICALLY ENCODED POSITION MULTIPLE-POINT SCINTILLATION DETECTOR USING A SINGLE COLLECTING LIGHT GUIDE

(75) Inventors: Francois Therriault-Proulx, Quebec (CA); Luc Beaulieu, Quebec (CA); Louis Archambault, Quebec (CA); Sam Beddar, Houston, TX (US)

(73) Assignees: Université Laval, Québec (CA); Board of Regents, The University of Texas System, Austin, TX (US)

( * ) Notice: Subject to any disclaimer, the term of this patent is extended or adjusted under 35 U.S.C. 154(b) by 113 days.

(21) Appl. No.: 14/122,013

(22) PCT Filed: May 24, 2012

(86) PCT No.: PCT/CA2012/000490
§ 371 (c)(1),
(2), (4) Date: Jun. 3, 2014

(87) PCT Pub. No.: WO2012/159201
PCT Pub. Date: Nov. 29, 2012

(65) Prior Publication Data
US 2014/0263991 A1    Sep. 18, 2014

Related U.S. Application Data

(60) Provisional application No. 61/489,639, filed on May 24, 2011.

(51) Int. Cl.
*G01T 1/10* (2006.01)
*G01T 1/161* (2006.01)
(Continued)

(52) U.S. Cl.
CPC .............. *G01T 1/10* (2013.01); *A61N 5/1071* (2013.01); *G01T 1/161* (2013.01); *G01T 1/2002* (2013.01); *G01T 1/2006* (2013.01); *G01T 1/2008* (2013.01)

(58) Field of Classification Search
CPC   G01T 1/20; G01T 1/2002; G01T 3/06; G01T 1/02; G01T 1/10; G01T 1/203
See application file for complete search history.

(56) References Cited

U.S. PATENT DOCUMENTS 4,471,223 A  *  9/1984  Hurst et al. ................ 250/357.1
5,006,714 A     4/1991  Attix
(Continued)

FOREIGN PATENT DOCUMENTS

EP            0947855         6/1999

OTHER PUBLICATIONS

WIPO, International Search Report and Written Opinion of PCT/CA2012/000490, mailed Aug. 15, 2012.

*Primary Examiner* — Marcus Taningco

(57) ABSTRACT

Various embodiments are described herein for a radiation dosimetry apparatus and associated methods for measuring radiation dose. In some embodiments, the apparatus includes multiple scintillating elements for detecting amounts of radiation dose at multiple points within a detection region. Each of the scintillating elements generates light in response to radiation interacting within their volume. A light guide combines the light generated by all of the scintillating elements as well as radiation-induced contaminated optical energy and transmits the combined light to a spectral analysis setup. Multi or hyper-spectral calibration technique allows calculating the dose or dose rate at the positions of the different scintillating elements. The calibration technique isolates the light produced by a given scintillating
(Continued)

element from the other scintillating elements as well as any other source of radiation-induced contaminating light.

16 Claims, 6 Drawing Sheets

(51) Int. Cl.
*A61N 5/10* (2006.01)
*G01T 1/20* (2006.01)

(56) References Cited

U.S. PATENT DOCUMENTS

| | | | |
|---|---|---|---|
| 6,285,740 B1 * | 9/2001 | Seely et al. | 378/98.9 |
| 6,313,465 B1 * | 11/2001 | Nittoh et al. | 250/370.11 |
| 6,522,403 B2 | 2/2003 | Wilson et al. | |
| 7,154,097 B2 * | 12/2006 | Fontbonne et al. | 250/368 |
| 7,442,932 B2 * | 10/2008 | Schultz et al. | 250/338.1 |
| 2007/0129593 A1 | 6/2007 | Gueye et al. | |
| 2009/0236510 A1 | 9/2009 | Lacroix et al. | |
| 2010/0038547 A1 | 2/2010 | Ishikawa | |
| 2010/0253941 A1 | 10/2010 | Brady et al. | |
| 2010/0270462 A1 | 10/2010 | Nelson et al. | |
| 2010/0288934 A1 | 11/2010 | Keppel et al. | |

* cited by examiner

METHODS AND APPARATUS FOR OPTICALLY ENCODED POSITION MULTIPLE-POINT SCINTILLATION DETECTOR USING A SINGLE COLLECTING LIGHT GUIDE

RELATED APPLICATIONS

This application claims the benefit of U.S. Provisional Patent Application No. 61/489,639 filed May 24, 2011, the entire contents of which are hereby incorporated by reference herein for all purposes.

FIELD

Various embodiments are described herein relating to apparatus and methods for determining radiation doses at multiple points within one or multiple detection regions coupled to a single collecting light guide.

INTRODUCTION

Plastic scintillation detectors have been used for dose measurement in radiation therapy due to their advantageous characteristics over other types of radiation detectors. For example, the water equivalence of plastic scintillation detectors allows for their use without perturbation of the radiation field. The scintillating element of plastic scintillation detectors also emits light proportionally to the radiation dose striking it in a nanosecond time-scale allowing for a rapid read-out. The response characteristics of plastic scintillation detectors are also known to be dose-rate independent, as well as independent of energy (from 0.2 to 25 MeV) and temperature. Plastic scintillation detectors can also have a diameter in the sub-millimeter range which may allow for their use for in vivo dosimetry during radiation therapy treatment. These detectors can also be used for quality assurance of a radiation beam prior to treatment delivery.

All of the radiation dosimetry systems proposed thus far that use multiple scintillation detectors require one non-scintillating collecting light guide per scintillating element. Therefore, measuring radiation dose at multiple points requires the use of as many collection optical fibers as there are scintillating elements, which makes the development of systems based on these detectors bulky and sometimes impractical or even impossible to achieve in practice. Accordingly, even if these detectors demonstrate better properties than other types of detector arrays, the deficient aesthetics and increased cost of having to use many collection optical fibers for an array of plastic scintillation detectors is a barrier to their use in a clinical product. The fact that only a single scintillating element can be used per collecting light guide also restrains the number of detectors that can be inserted inside a limited space, such as, for example, inside catheters or other apparatuses that could be used for in vivo dosimetry.

SUMMARY OF SOME EMBODIMENTS

In one aspect, at least one embodiment described herein provides a radiation dosimeter for measuring radiation dose at multiple points within a detection region. The radiation dosimeter includes a radiation detector comprising a plurality of scintillating elements located within the detection region and configured to generate optical energy in response to irradiation in the detection region, a single collecting light guide optically coupled to the radiation detector and configured to receive and transmit the optical energy generated by the plurality of scintillating elements, a spectral filter stage optically coupled to the single collecting light guide and configured to receive and spectrally decouple the transmitted optical energy, a photo-detector stage optically coupled to the spectral filter stage and configured to generate electrical signals indicative of optical energy within at least one region of the spectrally decoupled optical energy, and a computing device connected to the photo-detector stage and configured to receive and process the electrical signals to compute the measured radiation dose.

In at least one embodiment, the plurality of scintillating elements can be contiguous.

In at least one embodiment, the plurality of scintillating elements are coupled through non-scintillating optical fibers.

In at least one embodiment, at least one of the scintillating elements comprises water-equivalent materials.

In at least one embodiment, the components within the detection region comprise water-equivalent materials.

In at least one embodiment, the plurality of scintillating elements have different optical emission spectra.

In at least one embodiment, the plurality of scintillating elements are identical and the radiation detector further comprises a plurality of band-pass filters coupled in between the plurality of scintillating elements and having different pass bands to produce different optical emission spectra.

In at least one embodiment, the radiation detector comprises a one or more scintillating rods having an optical emission spectrum that varies along its length to provide the plurality of scintillating elements.

In at least one embodiment, the plurality of scintillating elements with different optical emission spectra are produced through the alteration of a common scintillating element.

In at least one embodiment, the spectral filter stage comprises a plurality of splitters with a final stage coupled to a plurality of downstream transmission optical filters.

In at least one embodiment, the spectral filter stage comprises a small aperture element coupled to a downstream dispersion prism.

In at least one embodiment, the spectral filter stage comprises a small aperture element coupled to a downstream optical grating.

In at least one embodiment, the plurality of scintillating elements are arranged in a linear configuration.

In at least one embodiment, the plurality of scintillating elements are arranged in a two-dimensional planar configuration.

In at least one embodiment, the plurality of scintillating elements are arranged in a three-dimensional configuration.

In another aspect, at least one embodiment described herein relates to a method of calibrating a radiation dosimeter comprising a single collecting optical fiber and a plurality of scintillating elements with different optical emission spectra. The method may include:

a) determining a number (L) of spectral bands corresponding to a number (N) of optical energy emitting elements including scintillating and contaminating elements, wherein $L \geq N$, b) irradiating at least one of the optical energy emitting elements with an irradiation condition for which the dose to a particular scintillating element is known, c) measuring an electrical signal corresponding to each of the L different spectral bands for this irradiation condition to form one row of a measurement matrix M, d) repeating the irradiating and measuring steps for an additional K-1 known different irradiation conditions where K≤L to obtain the remaining rows of matrix M, e) solving for the calibration factors for this scintillating element; and f) repeating steps b to e for the remaining optical energy emitting elements.

In some embodiments, the plurality of radiation-induced optical energy emitting elements comprises a plurality of scintillating elements.

In some embodiments, the plurality of radiation-induced optical energy emitting elements comprises a plurality of contaminating radiation-induced optical elements.

In some embodiments, the plurality of radiation-induced optical energy emitting elements comprises a plurality of scintillating elements and a plurality of contaminating radiation induced elements.

BRIEF DESCRIPTION OF THE DRAWINGS

For a better understanding of the various embodiments described herein and to show more clearly how they may be carried into effect, reference will now be made, by way of example only, to the accompanying drawings in which.

DESCRIPTION OF SOME EMBODIMENTS

Figure 1:
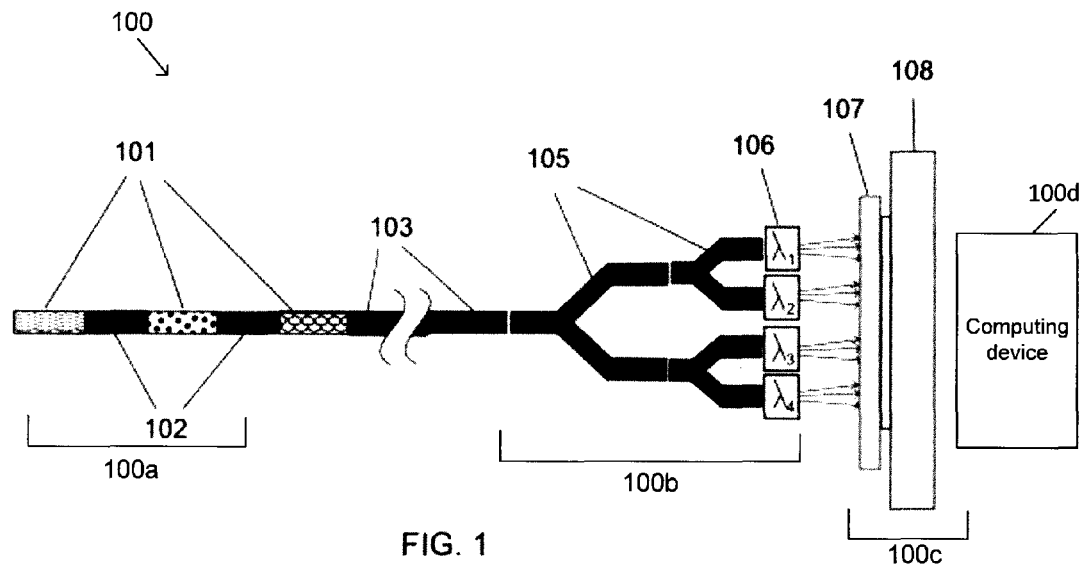
FIG. 1 is a schematic side view of one example embodiment of a radiation dosimeter.

It will be appreciated that numerous specific details are set forth in order to provide a thorough understanding of the various embodiments described herein. However, it will be understood by those of ordinary skill in the art that the various embodiments may be implemented without these specific details. In other instances, well-known methods, procedures and components have not been described in detail so as not to obscure the embodiments described herein. Furthermore, where considered appropriate, reference numerals may be repeated among the figures to indicate corresponding or analogous elements.

Various embodiments of apparatuses and corresponding methods are described herein, at least one of which may provide a more practical, clinically viable implementation of multi-point radiation dosimetry.

In general, radiation dosimeters in accordance with the teachings herein may employ a multi-point plastic scintillation detector coupled to a single light collecting guide whose output goes through an optical spectral separation and filtration arrangement before being measured at a photo-detector stage, which may be an array of photo-detectors in some cases. The multi-point scintillation detector has numerous scintillating elements that can be coupled together on a common optical conduit.

The radiation dose that is delivered to the scintillating elements can be calculated by combining the output of the scintillating elements, which are in different spectral bands, and performing measurements in the different spectral bands which are then adjusted by calibration factors.

Figure 3:
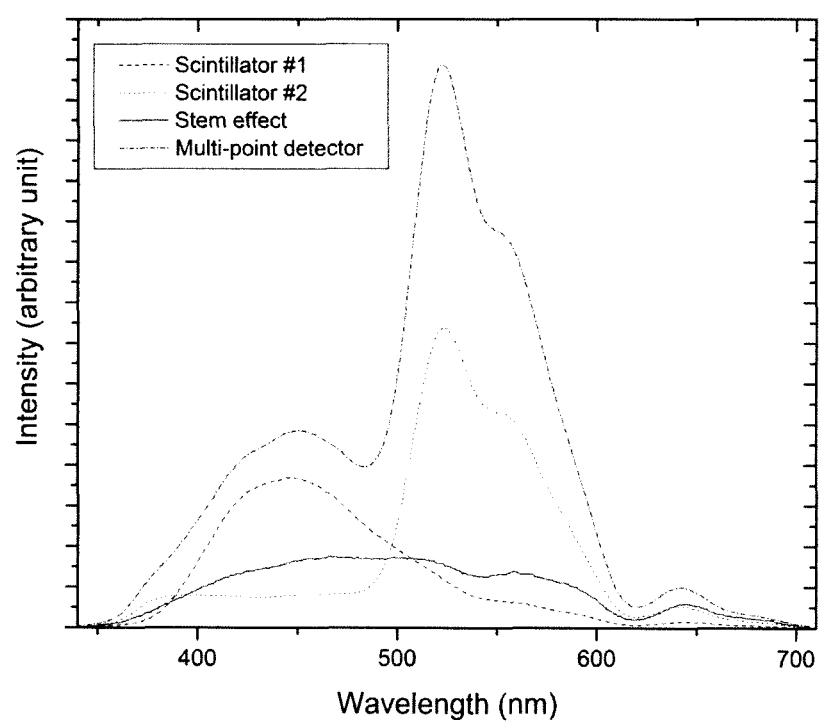
FIG. 3 is an example representation of the emission spectrum of three different light emitting components along with the spectrum of their sum as expected in a multi-point scintillation detector.

There may be some overlap in the different spectral bands especially in the case of contaminating signals which have a broad continuous spectrum (see FIG. 3 for example). The overlap is generally acceptable as long as the spectra of interest from the scintillating elements produce distinct responses that are discernible from one another. Furthermore, in general, this type of arrangement retains the advantages of plastic scintillation detectors over other types of detectors while being more clinically practical.

Referring now to FIG. 1, shown therein is an example embodiment of a radiation dosimeter 100 comprising a radiation detector 100a, a single collecting light guide 103, a spectral filter stage 100b, a photo-detector stage 100c, and a computing device 100d. In some embodiments, the radiation dosimeter 100 can be shielded from external light by using a black jacket (not shown) or other shielding device around the scintillating elements 101 and the light guides 102 and 103, as well as an enclosure (not shown) between the spectral filter stage 100b and the photo-detector stage 100c.

The radiation detector 100a is a multi-point plastic scintillation detector that has multiple plastic scintillating elements 101 coupled to each other through the light guides 102, which can be plastic and sized to correspond with a detection region within which the radiation dosimeter 100 is placed to detect a radiation dose during use. Accordingly, the light guides 102 can be short in length.

In this example embodiment, the scintillating elements 101 have different light emission spectra. While three scintillating elements 101 are shown, this is for illustrative purposes only and one skilled in the art will understand that a different number of scintillating elements may be used.

During operation, the radiation detector 100a is irradiated and light is generated by the scintillating elements 101 in an amount proportional to the radiation dose that strikes the active area of the scintillating elements 101.

In some embodiments, typical dimensions for the scintillating elements 101 may include a diameter of about 0.5 to 1 mm and a length of about 1-5 mm, while typical dimensions for the light guides 102 may include a similar diameter as the scintillating elements 101 and a minimum length of about 1 mm to a maximum length that depends on the desired position of the scintillating elements 101.

In some embodiments, one or more components may have other shapes and sizes. In particular, one or more of the scintillating elements 101, light guides 102, 103, optical fibers 106, and optical splitters 105 may have other cross sectional shapes, such as square cross sections, elliptical cross sections, or other cross sectional shapes. In some embodiments, one or more of the scintillating elements 101, light guides 102, 103, optical fibers 106, and optical splitters 105 may have different cross sections from each other (e.g., scintillating elements 101 may have square cross sections, while light guides 102, 103 may have round cross sections).

Some example materials that can be used for the scintillating elements 101 include, but are not limited to, organic (plastic) materials such as polystyrene and polyvinyltoluene, as well as inorganic materials such as, but not limited to, Sodium Iodide (NaI), Bismuth Germanate (BGO), Caesium Iodide (CsI), Calcium Fluoride ($CaF_2$), Aluminum Oxide ($Al_2O_3$) and the like.

The light guides 102 can be made of organic materials such as, but not limited to, Polymethyl methacrylate (PMMA) as well as inorganic materials such as, but not limited to, silica, and light guiding capillary tubing.

The arrangement of scintillating elements 101 and the light guides 102 is coupled to a single collecting light guide 103. In use, the scintillating elements 101 generate optical energy in response to irradiation in the detection region. The single collecting light guide 103 receives and transmits the generated optical energy as an optical signal to the spectral filter stage 100b, which is a setup that provides for the spectral division of the optical signal.

The light output from the single light guide 103 is composed of the sum of light produced by the scintillating elements 101 as well as other sources, as explained below. The spectral filter stage 100b includes one or more optical splitters 105 that split the optical signal along a plurality of branches.

In some embodiments, the optical signal is split in a ratio according to the number of branches. In other embodiments, the optical signal may be split according to a different ratio (e.g. 90% on one branch, 10% on another branch, and so on). In particular, the ratio need not be inversely proportional to the number of branches, although this could be one option.

In some embodiments, multiple levels of splitters can be used to allow for separation of the optical signal into a desired number of optical beam outputs.

Each of the outputs from the last stage of the optical splitters 105 passes through a plurality of transmission optical filters 106. The number of splitters within the optical splitter 105 and the number of transmission optical filters 106 generally depends on the number of scintillating elements 101 as well as the number of other radiation-induced contaminating sources that have to be dealt with.

Indeed, in addition to the multiple scintillating elements 101, the radiation dosimeter 100 normally has to account for other types of radiation-induced light that are produced inside any transparent medium as in the case of the non-scintillating light guides 102. For example, Cerenkov radiation and fluorescence are among the known sources of radiation-induced light that may have to be taken into account depending on the specific application of the radiation dosimeter 100. However, these additional light emitting sources can be dealt with in the same manner as the scintillating elements 101.

Accordingly, each of the transmission optical filters 106 may possess a unique transmission spectrum that is suited more or less to the spectrum of one specific light emitting element.

The photo-detector stage 100c may also include an objective lens system 107 that collects the output energy from the spectral filter stage 100b and projects a corresponding image on the photosensitive surfaces of a photo-detector array 108, such as a CCD camera for example. The image normally includes a plurality of optical beams which each correspond to one of the transmission optical filters 106. Persons skilled in the art will understand that other photo-detector arrays can be used such as, but not limited to, photo-multiplying tubes, photodiodes, CMOS cameras, EMCCD, ICCD, a spectrometer, and so on.

In this embodiment, the resulting optical beams are imaged at separate locations on the photo-detector array 108, which converts the light intensity striking each of its photo-detectors into an electrical signal. The electrical signals generated from the photo-detectors that correspond to the same optical beam from the spectral filter stage 100b can be summed together to produce one integrated value.

The electrical signals from the photo-detector stage 100c may thereafter be processed by the computing device 100d, such that these signals may be combined and converted to a measurement of the radiation dose that is deposited within each of the scintillating elements 101.

The computing device 100d receives the electrical signals generated by the photo-detector stage 108 and processes these electrical signals to determine various information, such as the overall radiation dose D in the detection region or the radiation dose that is measured at a given scintillating element 101 as described in more detail below.

In this example embodiment, the computing device 100d is configured to combine the electrical signals corresponding to a particular beam into one integrated value.

In some embodiments, the computing device 100d can be a desktop computer, laptop, tablet or other handheld computing device that receives the electrical signals from the photo-detector stage 108 and processes the signals. Accordingly, the computing device 100d can be connected to the photo-detector stage 108 using an appropriate connection, such as a coaxial cable, a USB cable, or even via a wireless signal as the case may be.

In some cases, the computing device 100d can be a processor that is included with the photo-detector stage 108. In other cases, the computing device 100d can include custom circuitry or dedicated hardware that is designed to perform the required calculations.

In this multi-point scintillation-based radiation dosimeter 100, the overall optical spectrum is a linear superposition of N distinct spectra having intensities $I_n$ (see equation 1). Referring now to FIG. 3, shown therein is an example representation of an emission spectrum from three different light emitting components comprising two scintillating elements (scintillators #1 and #2) and a contaminating component from a contaminating source in a non-scintillating light guide. This contaminating component may also be referred to as the stem effect.

An example spectrum obtained from irradiation of a multi-point scintillation detector composed of scintillators #1 and #2 and a single collecting light guide is also represented and shows that the light output from this detector is a combination of the light emitted by the stem effect and both scintillating elements.

$$I = [I_1 I_2 \ldots I_N] \quad (1)$$

The measurement of a radiation dose within a detection region using a specific scintillating element 101 from the multi-point radiation detector 100a may be characterized as a linear combination of the light measured in different spectral bands regardless of whether the light comes from scintillating elements or other contaminating light, particularly radiation-induced contaminating light.

The number of different light emitting components defines the minimum number of spectral bands that are employed in the radiation dosimeter 100. The combined response $R_{n,l}$ of filtering elements 106 and photo-detector stage 100c is specific to each spectral band and differs for each light emitting component since the emission spectra are unique. Accordingly, the response to N radiation-induced light emitting elements in L spectral bands is given by equation 2.

$$R = \begin{bmatrix} R_{1,1} & R_{1,2} & \cdots & R_{1,L} \\ R_{2,1} & \ddots & & \\ \vdots & & & \\ R_{N,1} & & & R_{N,L} \end{bmatrix} \quad (2)$$

Measurements (M) are made with the radiation dosimeter 100 so that there is a measurement for each spectral band as shown in equation 3.

$$M = I \cdot R = \begin{bmatrix} \sum_{i=1}^{N} I_i R_{i,1} & \cdots & \sum_{i=1}^{N} I_i R_{i,L} \end{bmatrix} \quad (3)$$

If one of the spectral components, $I_D$, is from a scintillation element 101 and is proportional to a radiation dose (D) of interest, the radiation dose (D) at the scintillation element can be measured according to equation 4:

$$D = \alpha \cdot I_D = M \cdot f \quad (4)$$

where f is a calibration vector. Calibration for this particular scintillating element can be done by solving equation 4 for f when the radiation dose is known. This can be done by performing K measurements of known dose $D_k$, in which case M becomes a K×L matrix:

$$D = \begin{bmatrix} D_1 \\ D_2 \\ \vdots \\ D_K \end{bmatrix} \quad M = \begin{bmatrix} M_{1,1} & M_{1,2} & \cdots & M_{1,L} \\ M_{2,1} & \ddots & & \\ \vdots & & & \\ M_{K,1} & & & M_{K,L} \end{bmatrix} \quad f = \begin{bmatrix} f_1 \\ f_2 \\ \vdots \\ f_K \end{bmatrix}$$

Accordingly, the general solution of the calibration equation (D=Mf) is given by equation 5.

$$f = (M^T \cdot M)^{-1} \cdot M^T \cdot D \quad (5)$$

Equation 5 corresponds to the least-square estimation of f and requires K≥L. This formalism defines the calibration of a system with N spectra if L≥N.

In cases where K>L, the calibration equation can be solved by singular value decomposition, which should be numerically more robust than equation 5 to solve for f.

Regardless of which computational approach is utilized to solve the calibration equation, this calibration method can be applied separately to each of the scintillating elements 101 in order to determine their calibration factors.

This calibration method allows the radiation dose to be measured in a system with N-C scintillating components, where N is the number of light emitting components as defined above and C is the number of radiation-induced light contaminating components. Even if a minimum of L measurements need to be performed under known-dose conditions for each of the scintillating elements, the number of actual required measurements in practice should decrease as some of the conditions will be redundant for all scintillating elements as far as the dose is known to each of them. The total number of conditions required to calibrate all of the scintillating elements could be selected to be as low as L.

In practice, the choice of the calibration conditions will normally depend on the conditions in which the multi-point detector will be used. In general, calibration can be performed as follows:

Step 1: Irradiate a scintillating element of interest from the multi-point detector with in an irradiation condition for which the dose to this scintillating element is known.

Step 2: Measure the electrical signal in each of the L different spectral bands for this particular irradiation condition. Those measurements provide one row of the matrix M related to the dose at the same row number on matrix D.

Step 3: Repeat steps 1 and 2 for an additional K-1 conditions by making sure that every irradiation condition is different so that the relation between the doses received in each scintillating element of the multi-point detector is not a simple proportion of a previous calibration condition. The irradiation conditions can be made different by changing the radiation beam geometry, the detector position relative the radiation field, the type of radiation (i.e. electrons vs. photons) and the like as is known by those skilled in the art.

Step 4: Once all of the data for the M and D matrices are obtained, solve to get the calibration factors for this particular scintillating element.

Step 5: Repeat steps 1 to 4 for the N-C scintillating elements. However, it is important to note that the irradiations used to determine the calibration factors for the other scintillating elements could be used as far as the dose to these other scintillating elements are also known.

Once the calibration factors are obtained for each of the scintillating elements, the multi-point scintillation detector is ready to be used in a dosimeter under other irradiation conditions. Accordingly, there are calibration vectors f for each scintillating element of interest.

For example, given 4 scintillators and 1 contaminating signal, assuming 5 spectral bands are used, then after calibration is done, in use, the dose at scintillator #1 is given by equation 6:

Dose at scintillator #1=f1*M1+f2*M2+f3*M3+ f4*M4+f5*M5 (6)

where calibration factors f1 to f5 are specific to the dose calculation at scintillator #1. Similarly, the dose at scintillator #2 is given by equation 7:

Dose at scintillator #2=g1*M1+g2*M2+g3*M3+ g4*M4+g5*M5 (7)

where calibration factors g1 to g5 are specific to the dose calculation at scintillator #2. While calibrations factors f1 to f5 will be different from calibration factors g1 to g5, the measurements, M1 to M5, are the same in each equation.

In some embodiments, another method for calibrating a detector includes measuring or estimating the spectral response, R, of every element emitting optical energy for the L spectral bands. By knowing M and R (from equation 3), one can solve for I.

Then, at least one irradiation may be made with a known dose for each of the scintillating element to determine their signal response per unit dose (i.e. the parameter a in equation 4). In some embodiments, the same irradiation condition can be used for all of the scintillating elements. Equation 4 can then be used to determine the dose.

Figure 2:
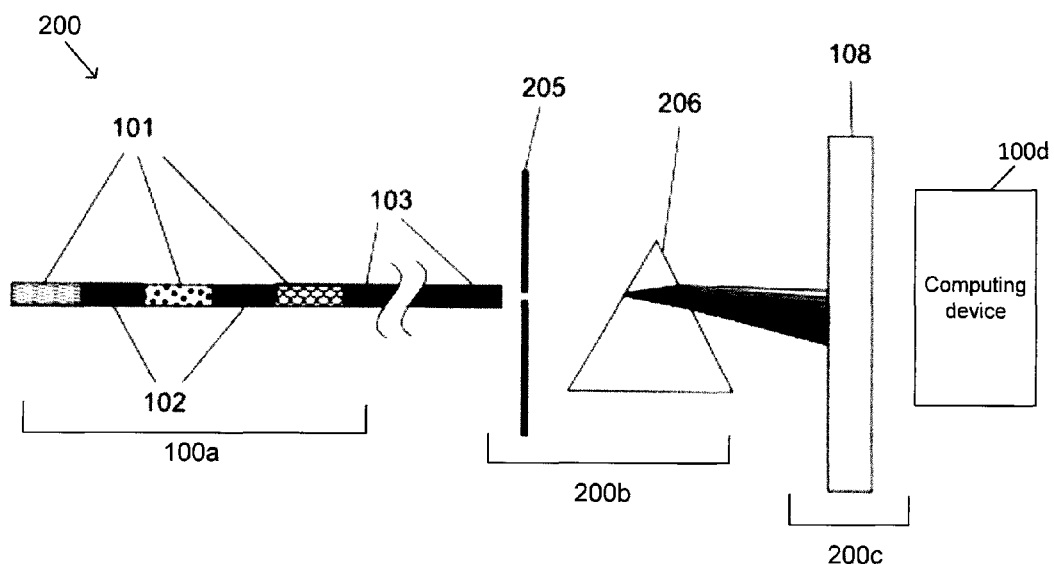
FIG. 2 is a schematic side view of another example embodiment of a radiation dosimeter.

Referring now to FIG. 2, shown therein is another example embodiment of a radiation dosimeter 200 that incorporates a light dispersion setup to perform spectral filtering. Accordingly, in this embodiment the radiation dosimeter 200 comprises a spectral filter stage 200b having a small aperture 205 and a prism 206.

In other embodiments, the aperture element 205 is optional depending on the actual implementation of the spectral filter stage.

The prism 206 is used to spatially and spectrally disperse the optical energy from the collecting light guide 103 into its many wavelength components. The spectrally dispersed light from the prism 206 is then collected by the photo-detector array 108. When the photo-detector array 108 is a CCD camera, each pixel of the camera along the direction of the spectrally dispersed light collects a different band of the light spectrum.

In a similar fashion to the radiation dosimeter 100, a finite number of spectral windows can be used in order to calculate the radiation dose delivered to a specific scintillating component using equation 4.

The different spectral windows may be defined by different selections of pixels along the dispersion direction. In comparison to the spectral division employed by the radiation dosimeter 100, the radiation dosimeter 200 may be more robust because a higher number of different spectral windows are available as each pixel represents a narrow spectral window. Using a larger number of spectral windows than the minimum required should lead to a better discrimination between the many light emitting components, although this is not required.

A person skilled in the art will understand that generally any array of suitable photo-detectors can be used for light measurement and that the radiation dosimeter 200 is therefore not limited to the use of a prism for dispersing light. Other suitable optical dispersion elements can be used, such as gratings for example.

In another alternative embodiment, at the expense of potentially higher cost, a spectrometer could be used to implement spectral filter stage 100b and photo-detector stage 100c in order to provide achieve light dispersion and photo-detection. The spectrometer may advantageously provide a better knowledge of the value of the wavelength of the light that strikes each pixel since it is calibrated beforehand.

In other embodiments, the spectral filter stage can be implemented with a time-varying optical filter device that has time-varying optical filter characteristics that can be changed over time, in which case the optical splitter 105 may not be required. This technique generally requires the changes in the optical filter characteristics to be faster than the time scale of the event of interest (i.e. the irradiation of the detection region).

In some embodiments, mechanical switching filters can be used for the time-varying optical filter. An example of a mechanical switching filter is an electro-mechanical filter wheel which is provided with a limited number of color filters mounted on a wheel. The light from the light collecting guide 103 may be passed through the wheel, which is turned to provide spectral filtering.

Electronically-tunable filters can also be used for the time-varying optical filter. Electronically-tunable filters may provide more rapid and non-sequential changing filter characteristics. Examples of electronically-tunable filters than can be used are liquid-crystal tunable filters (LCTF), acousto-optic tunable filters (AOTF), and Fabry-Perot devices (EOFP).

In another alternative embodiment, hyper-spectral snapshot imaging can be used for the photo-detector stage. This technique consists of the acquisition of an entire 2D image at multiple optical wavelengths in a single integration. This technique is particularly useful when using many multi-point scintillation detectors 100a. A Computed Tomography Imaging Spectrometer (CTIS), as described in U.S. Pat. No. 6,522,403, or a Coded Aperture Snapshot Spectral Imager (CASSI), as described in US Patent Application Publication No. 2010/0253941, can be used as the spectral filter and photo-detector stages.

A person skilled in the art will understand that there are various embodiments of the multi-point scintillation detectors and single collecting light guides described herein that can be used to provide many points of measurements or radiation dose assessment. For example, the radiation dosimeters 100 and 200 only show a small number of scintillating elements 101 for clarity of illustration. However, persons skilled in the art will understand that in various embodiments, many more scintillating elements 101 may be used. Furthermore, the use of short optical fibers (i.e. light guides 102) is optional. Both of these design parameters may depend on the desired geometry of the positions of interest for radiation dose measurement within the detection region.

Furthermore, a person skilled in the art will understand that while the embodiments described herein utilize plastic scintillating elements, other scintillating elements made of different materials can be used, as well as different types of non-scintillating light guide materials.

Figure 4A:
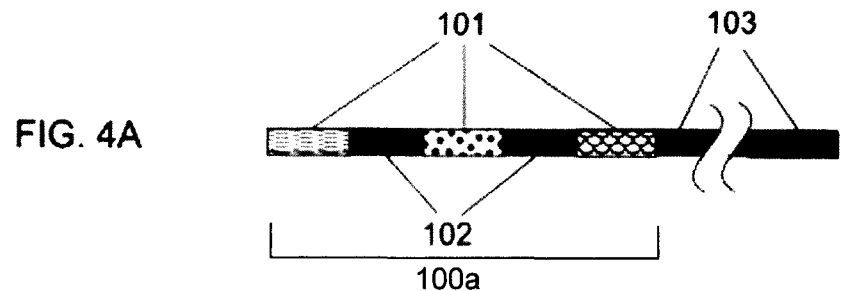
FIGS. 4A-4E show schematic side views of various embodiments of a radiation detector that can be used with the radiation dosimeters described herein.
Figure 4B:
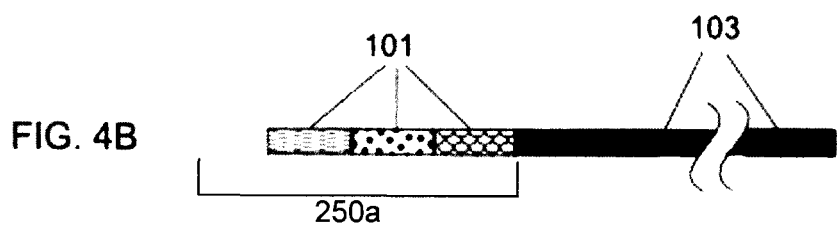
Figure 4C:
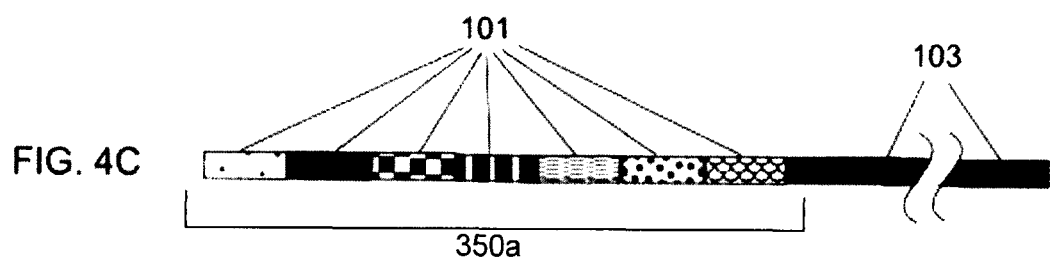

Referring now to FIGS. 4A to 4C, shown therein are various arrangements of multiple-scintillating elements that can be used in radiation detector according to various embodiments.

FIG. 4A shows a radiation detector 100a with several scintillating elements 101 that have different light emission spectra and are connected with short light guides 102.

FIG. 4B shows a radiation detector 250a with several scintillating elements 101 that have different light emission spectra and are connected to one another without the use of light guides 102.

FIG. 4C shows a radiation detector 350a that is similar to radiation detector 250a but with a higher number of scintillating elements 101 that have different emission spectra and are connected to one another without the use of light guides 102.

Figure 4D:
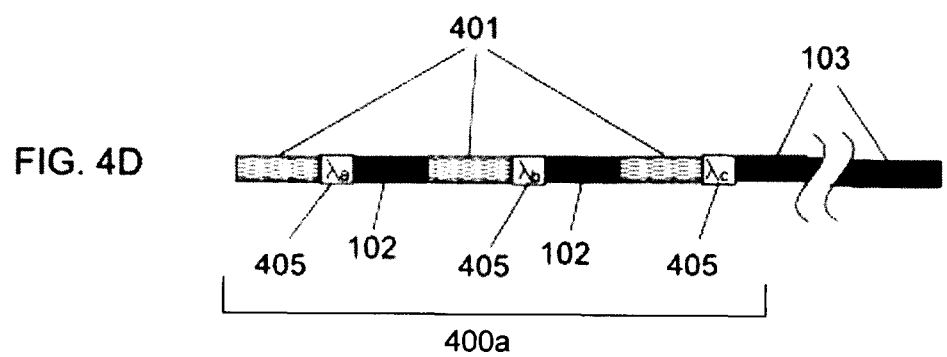

Referring now to FIG. 4D, shown therein is another alternative arrangement of scintillation elements that can be used in a radiation detector 400a. The radiation detector 400a comprises multiple scintillating elements 401 with similar emission spectra but they are each coupled to different band-pass optical filter 405 and light guides 102. The light guides 102 can be optional in some cases.

The band-pass filters 405 can be deposited as thin films in an optical fiber or may be in a different form as known by those skilled in the art.

The band-pass filters 405 have transmission spectra (i.e. pass bands) that are selected to transmit optical energy associated with the different regions of the scintillation spectrum of the scintillating elements 401. Accordingly, the pass bands are selected to be overlapping so that the emission spectra from all of the scintillating elements 401 can reach the single collecting light guide 103 but can be discriminated from one another.

For example, in one embodiment, all of the scintillating elements 401 have roughly the same emission spectra, but band-pass filter 405 has pass band $\lambda a$ from wavelengths w1 to w2, band-pass filter 405 has pass band $\lambda b$ from wavelengths w1 to w3 where w3>w2, band-pass filter 405 has pass band $\lambda c$ from wavelengths w1 to w4 where w4>w3 and so on and so forth. Other alternatives are possible.

In another embodiment, the original scintillation spectrum of a scintillating element could be physically altered in such a way that the emission spectra would be modified. This type of alteration could be performed many times in order to obtain many scintillators with different emission spectra, but all having been derived from a common type of scintillator. This could allow for using one or a few types of scintillators in order to obtain a higher number of scintillating elements with different emission spectra and then permitting their use within the same multi-point scintillation detector with a single collecting light guide.

Figure 4E:
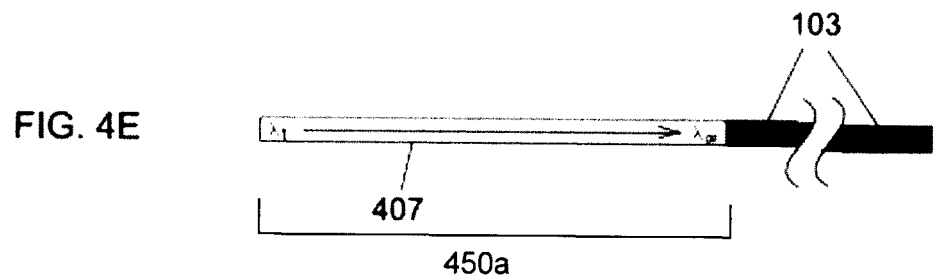

Referring now to FIG. 4E, shown therein is another embodiment of a radiation detector 450a which comprises a single scintillating element that can produce multiple emission spectra at different physical locations. The radiation detector 450a comprises a scintillating element 407 that can provide a changing light emission spectrum along its length.

For example, the scintillating element 407 can be a rod with a continuously changing light emission spectrum along its length. Such an arrangement decreases the number of optical coupling points and may considerably increases the already very good longitudinal spatial resolution of the radiation detector 450a.

In some embodiments, a rod may be much longer than a traditional scintillating element.

In some embodiments, a rod may be at least a centimeter in length. In some embodiments, a rod may be many centimeters in length.

There are various applications for the various multi-point radiation dosimeters described herein having multiple scintillating elements and a single collection optical fiber. These radiation dosimeters can be used as an easy to deploy straight-line detector to measure dose in the radiation field or in the penumbra of the radiation field.

They can also be used for a quick percent-depth-dose measurement of a radiation beam. In fact, one of the advantages of these radiation detectors is that the distance between the scintillating elements can be accurately measured and the scintillating elements can be arranged in a straight line which removes some geometrical uncertainties that are associated with using multiple, separate radiation detectors. This may be particularly true when using these radiation dosimeters for in-vivo dosimetry in which the radiation detector and single collecting optical fiber are inserted into a catheter or other type of enclosure with a limited amount of space to receive multiple radiation detectors.

The various embodiments of the multi-point radiation detector with a single collecting light guide described herein may also allow for a considerable decrease in the number of collection optical fibers in the construction of a 1D, 2D or 3D radiation detector array.

FIGS. 5-7 show example uses of the multi-point radiation detectors described herein to build up to a three-dimensional array of scintillating elements inside a water-equivalent phantom 503 when using multi-point scintillation detectors under a 1D (505), 2D (605) or 3D (705) configuration.

A person skilled in the art will understand that these are just some example geometries and that many other types of geometries can be used which incorporate the multi-point radiation detectors and single collecting light guide described herein.

Figure 5A:
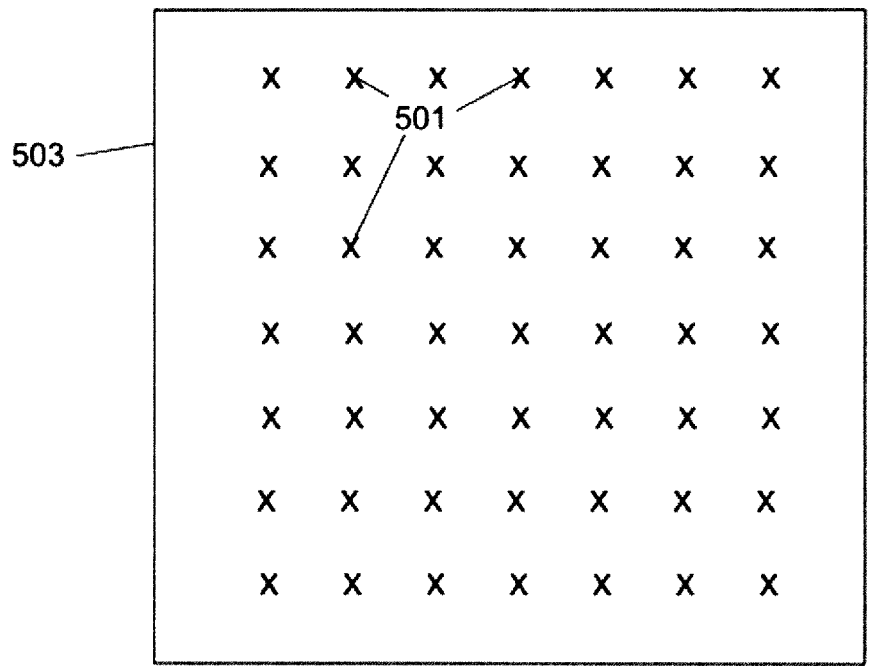
FIG. 5A is a schematic top view of a three-dimensional array of scintillating elements using a plurality of multi-point scintillation detectors in a 1D configuration.
Figure 5B:
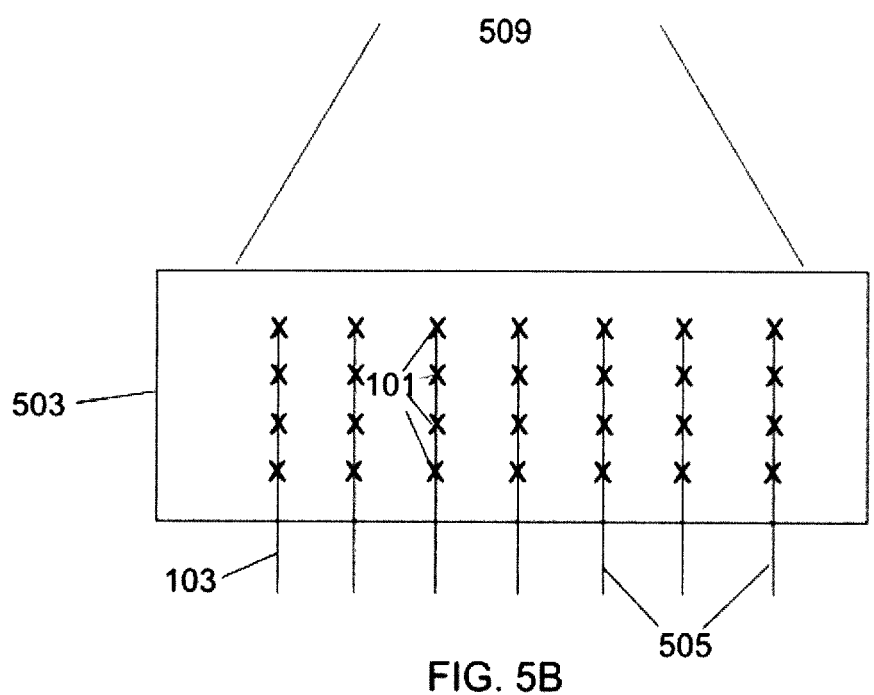
FIG. 5B is a schematic front view of a three-dimensional array of scintillating elements using a plurality of multi-point scintillation detectors in a 1D configuration.

FIGS. 5A to 6B show that several multi-point detectors can be used at the same time in order to perform a large number of dose measurements. In particular, FIGS. 5A and 5B shows a plurality of radiation detectors 501, each having a plurality of scintillating elements 101 and connected to a separate light collecting guide 103 in a 1-D configuration 505.

Figure 6A:
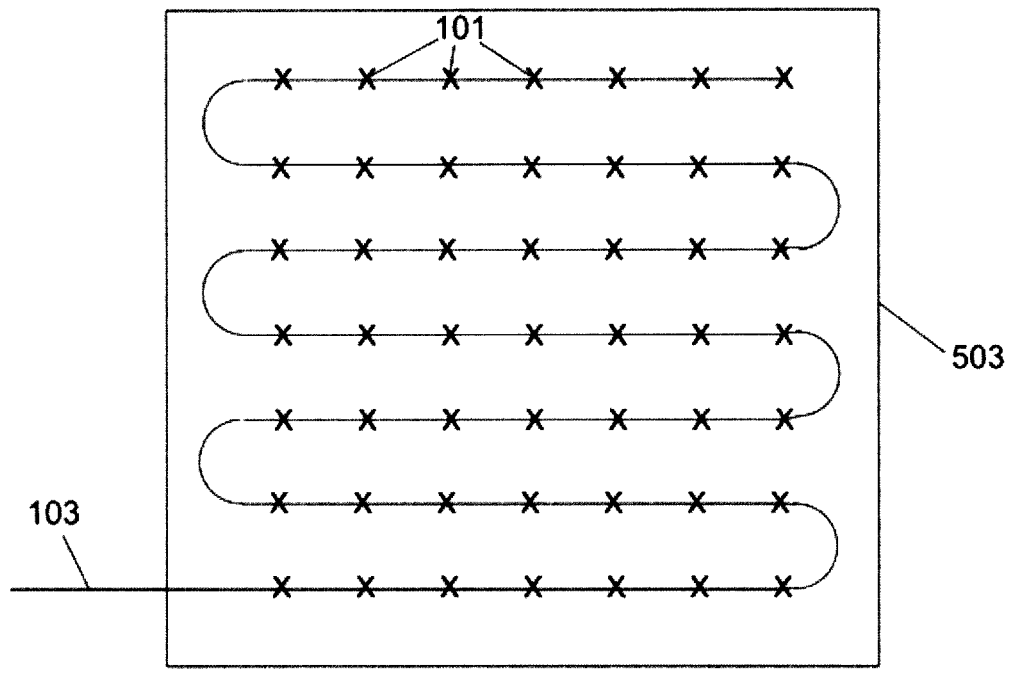
FIG. 6A is a schematic top view of a three-dimensional array of scintillating elements using a plurality of multi-point scintillation detectors in a 2D configuration.
Figure 6B:
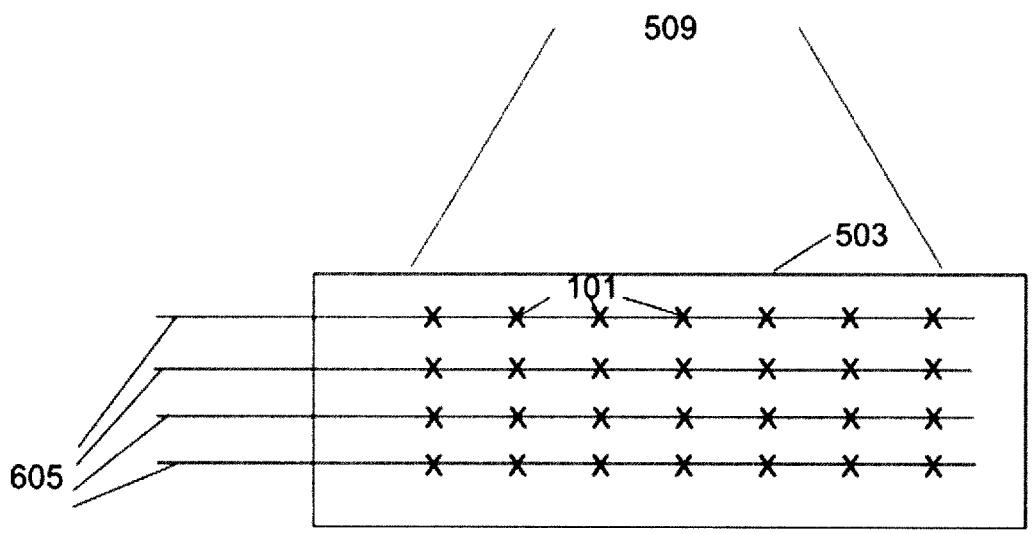
FIG. 6B is a schematic front view of a three-dimensional array of scintillating elements using a plurality of multi-point scintillation detectors in a 2D configuration.

FIGS. 6A and 6B show a plurality of radiation detectors each having a plurality of scintillating elements 101 arranged in a 2D configuration 605 along an x-y plane and connected to a separate light collecting guide 103.

Generally, the multi-point detectors can be placed either parallel to a radiation beam direction 509 (as in FIG. 5B) or perpendicular to the beam direction 509 (as in FIG. 6B). In both of these cases the radiation direction 509 is perpendicular to the plane of the figure and the figures are meant to show the radiation beam heading into the plane of the figure.

It should be understood that the orientation of the multi-point detectors with respect to the radiation beam direction is not limited to these cases and other orientations can be used.

Figure 7A:
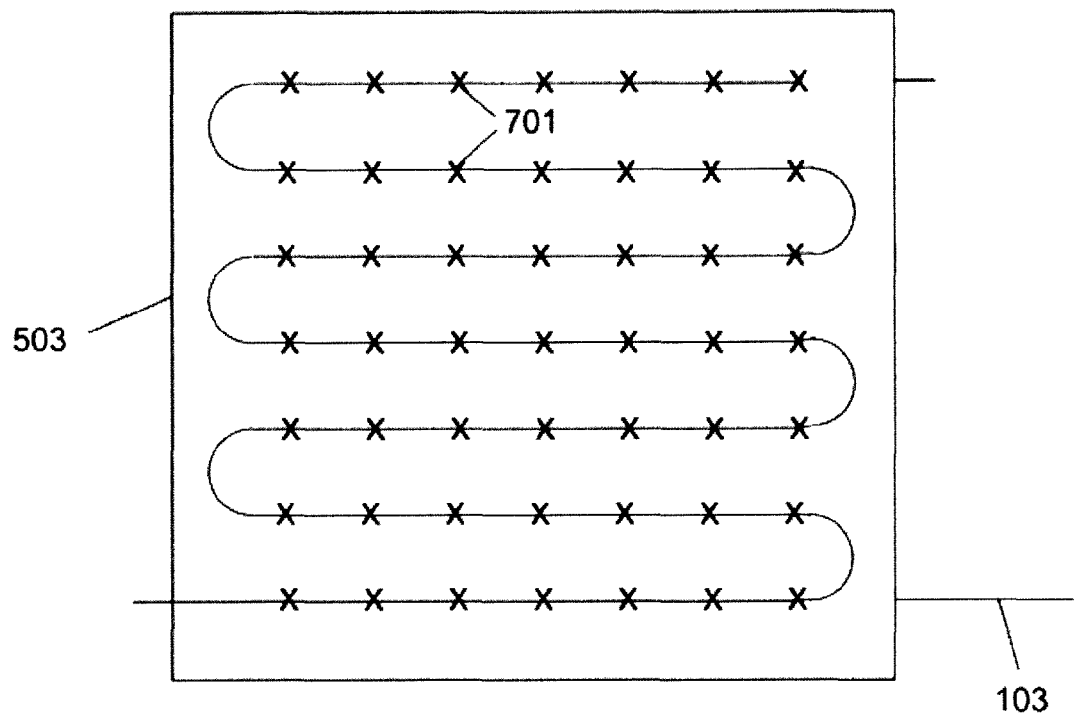
FIG. 7A is a schematic top view of a three-dimensional array of scintillating elements using a single multi-point scintillation detector in a 3D configuration.
Figure 7B:
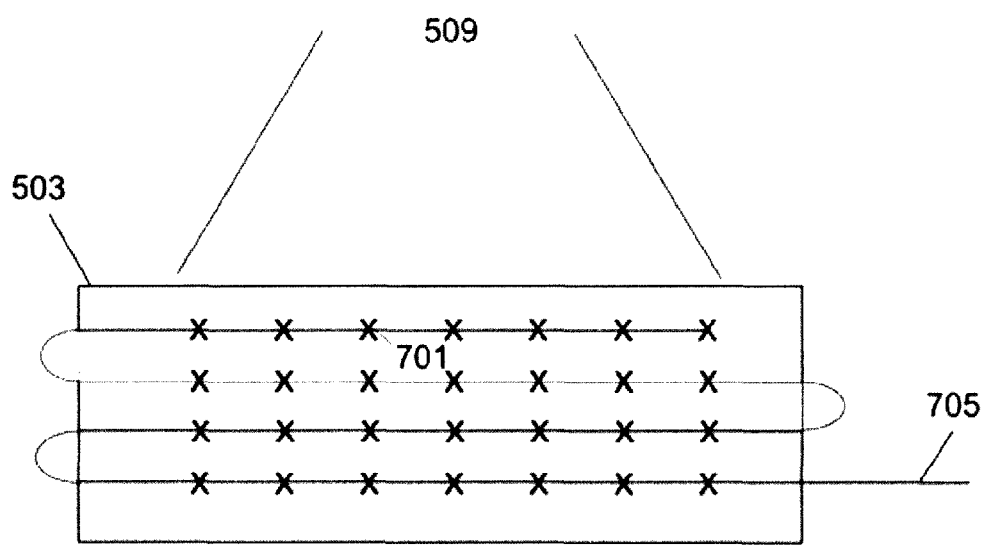
FIG. 7B is a schematic front view of a three-dimensional array of scintillating elements using a single multi-point scintillation detector in a 3D configuration.

Another result can also be achieved with a single multi-point detector as shown in FIGS. 7A and 7B in which a radiation detector 701 has scintillating elements arranged in a 3-D configuration 705 by connecting each 2-D planar configuration along a common optical conduit and then to the optical collecting guide 103.

The various embodiments of radiation dosimeters described herein may provide several advantages over existing techniques. Some of these advantages may include: 1) obtaining multiple dose points from a single detector in situations where access to the detection region is limited, 2) increasing the practicality of multiple point radiation dose measurements and applications, 3) decreasing the number of collecting light guides necessary to build 1D, 2D, or 3D arrays of radiation detectors, 4) decreasing the cost of multi-point detector radiation dosimeters, and/or 5) implementation of water equivalent detectors. Furthermore, the radiation dosimeters proposed herein may be able to account not only for the Cerenkov component, but also for any other radiation-induced contaminating elements with different light emission spectra.

In one application, one or more of the teachings herein may be used for in vivo dosimetry, wherein at least a portion of a radiation dosimeter (e.g. a radiation detector) is inserted into a patient, and the patient is then irradiated.

The various embodiments described herein have been provided as examples only. It should be understood that various modifications in form and detail can be made to the embodiments described and illustrated herein, without departing from the appended claims.

The invention claimed is:

1. A radiation dosimeter for measuring radiation dose at multiple points within a detection region, wherein the radiation dosimeter comprises:

a radiation detector comprising a plurality of scintillating elements located within the detection region, each scintillating element configured to generate optical energy in a different region of a scintillation spectrum in response to irradiation at multiple points within the detection region, each of the plurality of scintillating elements being responsive to a same type of radiation;

a single collecting light guide optically coupled to the radiation detector and configured to receive and transmit the optical energy in the different regions of the scintillation spectrum generated by the plurality of scintillating elements;

a spectral filter stage optically coupled to the single collecting light guide and configured to receive and spectrally decouple the different regions of the scintillation spectrum in the transmitted optical energy;

a photo-detector stage optically coupled to the spectral filter stage and configured to generate electrical signals indicative of optical energy within at least one region of the spectrally decoupled optical energy; and a computing device connected to the photo-detector stage and configured to receive and process the electrical signals to compute the measured radiation dose.

2. The radiation dosimeter according to claim 1, wherein the plurality of scintillating elements are contiguous.

3. The radiation dosimeter according to claim 1, wherein the plurality of scintillating elements are coupled through non-scintillating optical fibers.

4. The radiation dosimeter according to claim 1, wherein at least one of the scintillating elements comprises water-equivalent materials.

5. The radiation dosimeter according to claim 1, wherein components within the detection region comprise water-equivalent materials.

6. The radiation dosimeter according to claim 1, wherein the plurality of scintillating elements have different optical emission spectra.

7. The radiation dosimeter according to claim 1, wherein the plurality of scintillating elements are identical and the radiation detector further comprises a plurality of band-pass filters coupled in between the plurality of scintillating elements and having different pass bands to produce different optical emission spectra.

8. The radiation dosimeter according to claim 1, wherein the radiation detector comprises a scintillating rod having an optical emission spectrum that varies along its length to provide the plurality of scintillating elements.

9. The radiation dosimeter according to claim 6, wherein the plurality of scintillating elements with different optical emission spectra are produced through the alteration of a common scintillating element.

10. The radiation dosimeter according to claim 1, wherein the spectral filter stage comprises a plurality of splitters with a final stage coupled to a plurality of downstream transmission optical filters.

11. The radiation dosimeter according to claim 1, wherein the spectral filter stage comprises a small aperture element coupled to a downstream dispersion prism.

12. The radiation dosimeter according to claim 1, wherein the spectral filter stage comprises a small aperture element coupled to a downstream optical grating.

13. The radiation dosimeter according to claim 1, wherein the plurality of scintillating elements are arranged in a linear configuration.

14. The radiation dosimeter according to claim 1, wherein the plurality of scintillating elements are arranged in a two-dimensional planar configuration.

15. The radiation dosimeter according to claim 1, wherein the plurality of scintillating elements are arranged in a three-dimensional configuration.

16. A radiation dosimeter for measuring radiation dose, comprising:
  a light guide;
  a plurality of scintillating elements coupled to the light guide, the scintillating elements located within the detection region, each scintillating element configured to generate optical energy in a different region of a scintillation spectrum in response to irradiation at multiple points within the detection region, each of the plurality of scintillating elements being responsive to a same type of radiation; and
  a spectral filter stage optically coupled to the light guide and configured to receive and spectrally decouple the different regions of the scintillation spectrum in transmitted optical energy generated by the plurality of scintillating elements.

* * * * *